United States Patent [19]
Ptchelintsev

[11] Patent Number: 5,866,147
[45] Date of Patent: Feb. 2, 1999

[54] ASCORBYL-PHOSPHORYL-CHOLESTEROL

[75] Inventor: Dmitri Ptchelintsev, Mahwah, N.J.

[73] Assignee: Avon Products, Inc., Suffern, N.Y.

[21] Appl. No.: 837,282

[22] Filed: Apr. 11, 1997

Related U.S. Application Data

[63] Continuation of Ser. No. 440,765, May 15, 1995, abandoned.
[51] Int. Cl.[6] ............................. A61K 7/00; A61K 31/375
[52] U.S. Cl. ........................... 424/401; 514/169; 514/474; 514/844; 514/944
[58] Field of Search ..................... 424/401, 59; 514/169, 514/474, 844, 944

[56] References Cited

U.S. PATENT DOCUMENTS

| | | |
|---|---|---|
| 3,151,127 | 9/1964 | Spanel . |
| 4,564,686 | 1/1986 | Ogata .................................... 549/220 |
| 4,939,128 | 7/1990 | Kato et al. ................................. 514/82 |
| 4,954,532 | 9/1990 | Elliott et al. . |
| 5,306,713 | 4/1994 | Suetsugu et al. ....................... 514/100 |
| 5,336,485 | 8/1994 | Fariss ....................................... 424/10 |
| 5,474,991 | 12/1995 | Ogata ..................................... 514/100 |

FOREIGN PATENT DOCUMENTS 92104149  9/1992  United Kingdom .

OTHER PUBLICATIONS

Menon et al., Structural Basis for the Barrier Abnormality Following Inhibition of HMG CoA Reductase in Murine Epidermis, J. Invest. Dermatol., vol. 98, pp. 209–219 (1992).

Steinhart et al., Pro–and Antioxidative Effect of Ascorbic Acid on L–Tryptophan in the System $FE^{3+}$ /Ascorbic Acid/ $O_2$, J. Agric. Food Chem., vol. 41, pp. 2275–2277 (1993).

Sakamoto et al., Measurement Method of Efficacy of Anti-dandruff Cosmetics and Development of the New Active Commercial Product, IFSCC, Yokohama, vol. B206, pp. 823–864 (1993.

*Primary Examiner*—Gollamudi S. Kishore
*Attorney, Agent, or Firm*—Ohlandt, Greeley, Ruggiero & Perle

[57] ABSTRACT

This disclosure relates to a novel derivative of L-ascorbic acid which is stable, easily incorporated into cosmetically acceptable vehicles and enzymatically bioreversible in the skin to free ascorbic acid and a safe cholesterol component. An exemplary embodiment is 3'-(L-ascorbyl-2-phosphoryl)-cholesterol which is shown in Formula I.

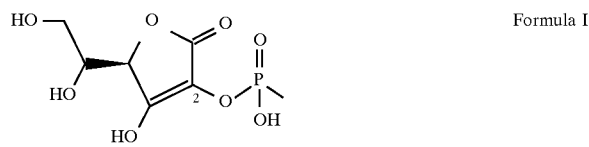

Formula I

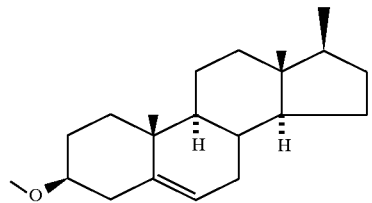

8 Claims, 1 Drawing Sheet

ASCORBYL-PHOSPHORYL-CHOLESTEROL

This is a continuation of application Ser. No. 08/440,765, filed May 15, 1995, now abandoned.

FIELD OF INVENTION

The present invention relates to synthesis and use of a novel derivative of L-ascorbic acid that is stable, easily incorporated into cosmetically acceptable vehicles and enzymatically bioreversible to its constituent components. Exemplary derivatives include 3'-(L-ascorbyl-2-phosphoryl)-cholesterol and 3'-(L-ascorbyl-3-phosphoryl)-cholesterol and salts thereof.

BACKGROUND OF THE RELATED ART

The use of L-ascorbic acid as an anti-oxidant in food preparations is known. For example, Steinhart, Pro- and Antioxidative Effect of Ascorbic Acid on L-Tryptophan in the System $Fe^{3}+$/Ascorbic Acid/$O_2$, J. Agric. Food Chem., Vol. 41, pages 2275–2277 (1993) describes the use of L-ascorbic acid as an anti-oxidant which performs its function in food by removing free radicals and undergoing rapid oxidation itself.

Similarly, free L-ascorbic acid in topical preparations demonstrates poor stability and tends to break down due to partially oxidative and non-oxidative degradation. The degraded ascorbic acid loses activity and the host product loses aesthetic appeal by exhibiting a brown color which is unacceptable for commercial cosmetics.

Although cholesterol, especially in the ingested form, is considered unhealthy, the benefits of cholesterol unassociated with L-ascorbic acid for skin barrier repair are known. For example, Menon, Structural Basis for the Barrier Abnormality Following Inhibition of HMG CoA Reductase in Murine Epidermis, J. Invest. Dermatol., Vol. 98, pages 209–219 (1992), describes deficiencies noted in the skin barrier repair mechanism when cholesterol synthesis is inhibited by down-regulation of HMG CoA reductase.

Mechanical mixing of L-ascorbic acid and cholesterol according to currently available methods results in a product which is also unstable due to the over-riding problem of L-ascorbic acid instability. For example, U.S. Pat. No. 4,939,128, at column 3, lines 21–22, describes ascorbic acid in conjunction with a cholestanyl group. The conspicuous absence of cholesterol and the specific mention of a cholestanyl group reflects a recognition, prior to the present disclosure, that conjugates of L-ascorbic acid and cholesterol were not practical or desired.

Attempts have also been made to conjugate ascorbic acid with a glycyrrhetic group as described in European Application No. 92104149.7; and with a tocopheryl group as indicated by U.S. Pat. No. 3,151,127. U.S. Pat. Nos. 4,564,686 and 5,306,713 also disclose tocopheryl ascorbyl phosphate as an anti-oxidant having the following structure.

Sakamoto, Measurement Method of Efficacy of Antidandruff Cosmetics and Development of the New Active Commercial Product, IFSCC, Yokohama, Vol. B206, pages 823–864 (1993) describes the use of tocopheryl coupled to L-ascorbic acid. The coupled tocopheryl is an anti-oxidant preservative for the ascorbyl group, but the use of the ascorbyl-tocopheryl as a skin therapeutic is questionable because, unlike cholesterol, tocopheryl is not a natural substrate for the skin.

The art requires a method for covalently and bioreversibly coupling cholesterol to L-ascorbic acid. The coupled molecule should be stable so that full functional activity is retained even after decoupling by naturally occurring acidic phosphatases in the skin. The beneficial properties of L-ascorbic acid would be provided, including increased collagen production and skin-lightening, combined with the benefits of released cholesterol for improved elasticity, resistance, tone and moisture retention of the skin.

OBJECTS OF THE INVENTION

It is an object of the present invention to provide a method for covalently and bioreversibly coupling cholesterol to L-ascorbic acid for stabilization of the resulting molecule.

Another object of the present invention is to provide a stable composition with multiple skin care benefits.

A further object of the present invention is to provide a derivative of L-ascorbic acid that is stable, easily carried in cosmetic vehicles and enzymatically bioreversible to free ascorbic acid and a safe cholesterol component.

Yet another object of the present invention is to provide stable cosmetic formulations that demonstrate extended shelf-life.

These and other objects will become evident from the disclosure provided below.

SUMMARY OF INVENTION

The present invention includes a method for coupling a molecule of L-ascorbic acid to a molecule of cholesterol through a bioreversible phosphate linkage at position 2 or 3 on the ascorbyl group and position 3' on the cholesteryl moiety. Resulting compositions are also contemplated by this invention. Exemplary compounds include functional or structural homologs of 3'-(L-ascorbyl-2-phosphoryl)-cholesterol (Formula I) such as 31'-(L-ascorbyl-3-phosphoryl)-cholesterol (Formula II). Both formulas are illustrated below.

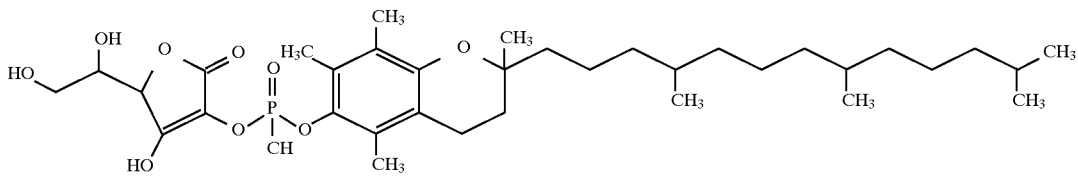

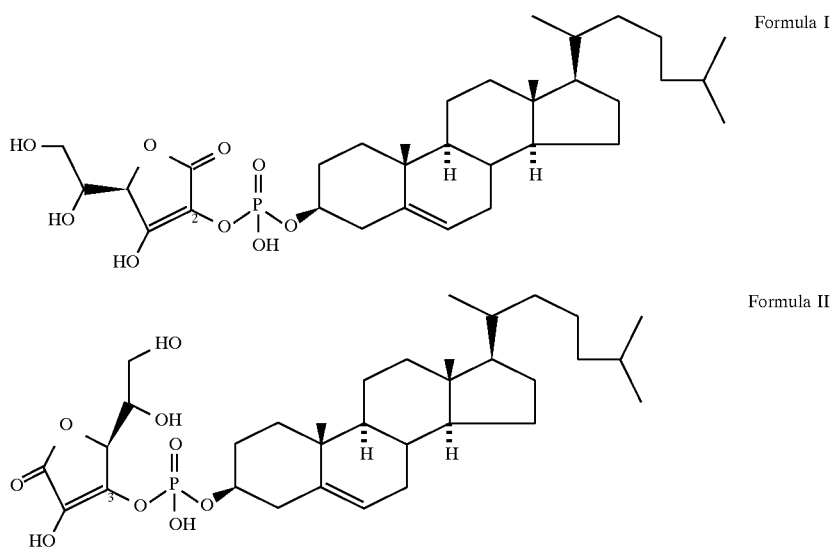

Formula I

Formula II

The conjugated 3'-(L-ascorbyl-2-phosphoryl)-cholesterol (Formula I) was prepared by dissolving cholesterol at −10° C. in dry diethyl ether (dried with 4A molecular sieves) containing 1.0 equivalent of triethylamine as a base. Phosphorous oxichloride (1.0 equivalent) was added to provide cholesteryl phosphorodichloridate.

The melting point of the cholesteryl phosphorodichloridate was measured as 121°–122° C. and infrared (KBr pellet) analysis showed P=O absorption at 1298 wavelengths and P—O—C absorption at 1019 wavelengths, with no hydroxyl absorption. Cholesteryl phosphorodichloridate was subsequently reacted for 3 hours at room temperature with 5,6-isopropylidene-L-ascorbic acid in tetrahydrofuran containing 1.0 equivalent of triethylamine. This reaction yielded a mixture of cholesteryl 5,6 isopropylidene-2-phosphorochloridate L-ascorbic acid and its isomer cholesteryl 5,6-isopropylidene-3-phosphorochloridate L-ascorbic acid.

The isomeric mixture was hydrolyzed in an aqueous solution of THF and stirred for several hours at room temperature with Amberlyst-15, a strongly acidic sulfonic acid ion exchange resin. THF and water were then removed and the final product, 3'-(L-ascorbyl-2-phosphoryl)-cholesterol, was extracted with ethyl acetate and neutralized with an KOH equivalent. The resulting solution was liophilized to obtain the monopotassium salt form.

This novel method permits covalent and bioreversible coupling of cholesterol with L-ascorbic acid resulting in the stabilization of ascorbic acid, as well as increased bioavailability for ascorbic acid and cholesterol. In the ascorbylphosphoryl-cholesterol compounds of the present invention the conjugated ascorbic acid becomes resistant to degradation. The cholesteryl group serves as a carrier moiety and facilitates delivery of polar ascorbic acid through the non-polar outermost protective layer of skin (i.e., the stratum corneum) and increases the bioavailability of the ascorbic acid in the topical application.

Natural enzymes, such as phosphatases present in the skin, gradually cleave the phosphate linkage between cholesterol and ascorbic acid, resulting in sustained release of free L-ascorbic acid and cholesterol into the stratum corneum. The released cholesterol is a natural substrate for skin and supplements that otherwise produced by the body. Topically applied cholesterol improves elasticity, tone and resistance to drying. A topical formulation of the present invention can comprise either 3'-(L-ascorbyl-2-phosphoryl)-cholesterol or 3'-(L-ascorbyl-3-phosphoryl)-cholesterol. In addition, ammonium, calcium, lithium, potassium or sodium salts of these compounds are readily incorporated into cosmetically acceptable vehicles. A salt with an organic amine such as ethanolamine will also provide the benefits intended by this invention.

Suitable vehicles include conventional lotions, creams or gels. A lotion embodiment may comprise about 0.1 to about 20.0% 3'-(L-ascorbyl-2-phosphoryl)-cholesterol or 3'-(L-ascorbyl-3-phosphoryl)-cholesterol, about 0.5 to about 6.0% glycerin, about 2.0 to about 8.0% propylene glycol dicaprylate/dicaprate, about 1.8 to about 4.0% Peg 40 Stearate, about 1.0 to about 2.5% Steareth-2, about 0.25 to about 0.7% xanthan gum, about 0.25 to about 0.7% hydroxyethyl cellulose, about 0.15 to about 0.2% disodium EDTA and about 0.20 to about 0.25% methylparaben with all ranges expressed as weight percents.

A cream embodiment may comprise about 0.1 to about 20.0% 3'-(L-ascorbyl-2-phosphoryl)-cholesterol or 3'-(L-ascorbyl- 3-phosphoryl)-cholesterol, about 0.5 to about 4.0% glycerin, about 2.0 to about 6.0% propylene glycol dicaprylate/dicaprate, about 1.8 to about 3.0% Steareth-20, about 0.8 to about 2.0% Steareth-2, about 0.25 to about 0.6% xanthan gum, about 0.25 to about 0.6% hydroxyethyl cellulose, about 1.0 to about 2.5% cetyl alcohol, about 0.9 to about 3.5% glycerol mono-stearate and about 0.15 to about 0.2% disodium EDTA.

A gel embodiment may comprise about 0.1 to about 20.0% 3'-(L-ascorbyl-2-phosphoryl)-cholesterol or 3'-(L-ascorbyl-3-phosphoryl)-cholesterol, about 0.15 to about 0.2% disodium EDTA, about 2.0 to about 6.0% propylene glycol, about 0.4 to about 1.5% hydroxyethyl cellulose and about 0.20 to about 0.25% methylparaben.

The pH of these formulations can be adjusted to physiologically acceptable levels with sufficient amounts of ammonium hydroxide, calcium hydroxide, lithium hydroxide, potassium hydroxide, sodium hydroxide, ethanolamine, diethanolamine or urea.

DETAILED DESCRIPTION OF THE INVENTION

Figure 1:
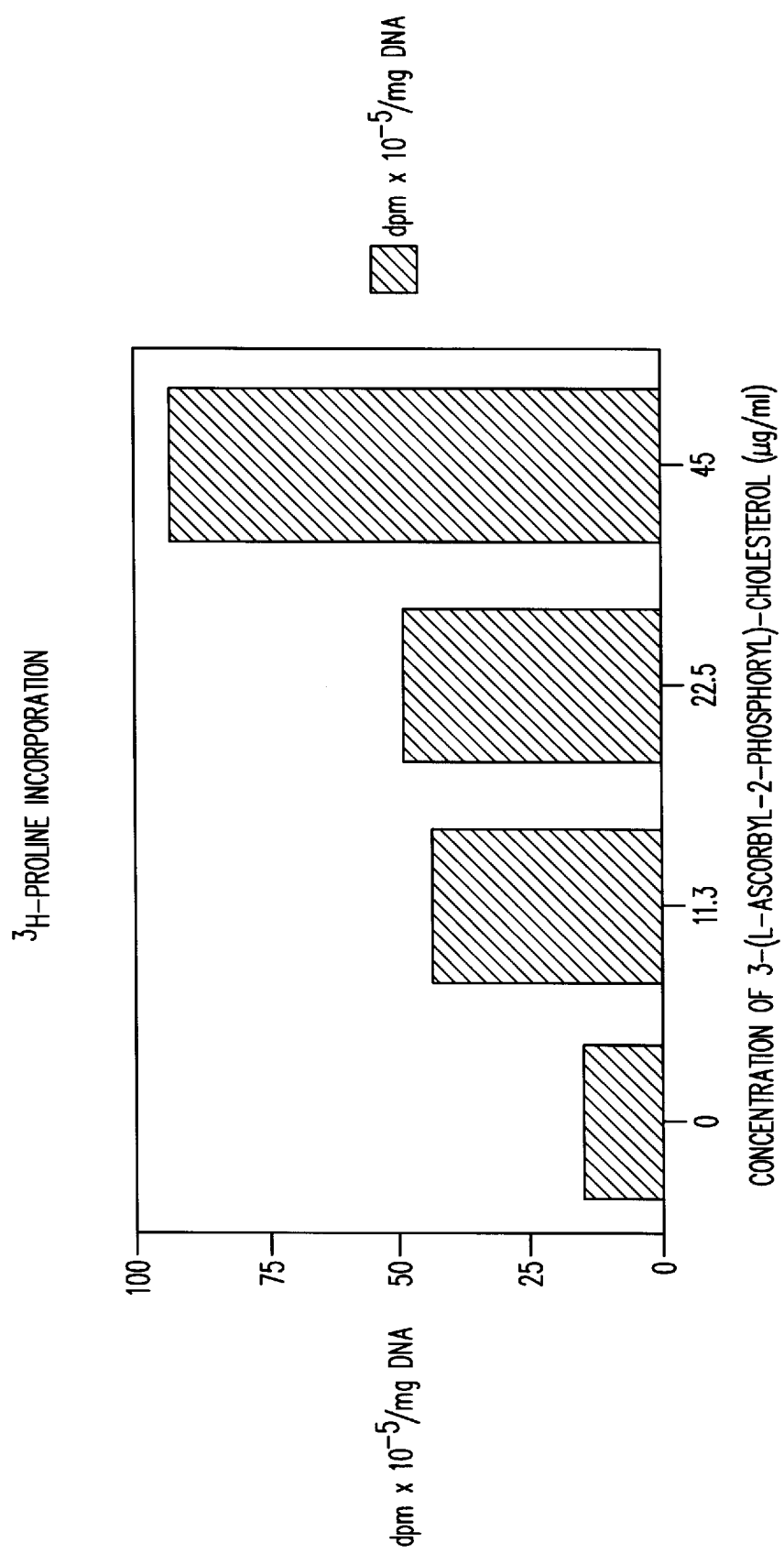
FIG. 1 illustrates that 3'-(L-ascorbyl-2-phosphoryl)-cholesterol increases production of new collagen by human fibroblasts in a dose dependent manner.

The compounds of the present invention are generally synthesized by (i) reacting cholesterol with a halogenophosphorelating agent, (ii) coupling the resulting product with 5,6-hydroxyl protected L-ascorbic acid, (iii) hydrolyzing the product with water, (iv) stripping the protective group with an acidic resin and (v) purifying the product with lyophilization and recrystalization. The derivative is stable in solution, exhibits anti-oxidant activity and stimulates production of collagen in fibroblasts.

EXAMPLE 1

Preparation of Phosphodiester Acid and its Mono Potassium Salt

Cholesteryl phosphodichloridate was synthesized using the following procedure. A 250 ml two neck 19/22 ST round bottom flask was selected for the reaction. It included a serum cap (with nitrogen inlet needle), a stirring bar and a 19/22 to 24/40 ST expansion adapter containing a 24/40 ST 125 ml dropping funnel equipped with a side arm. This apparatus was flame dried and cooled under a nitrogen sweep. The dropping funnel was charged with 4.64 grams (12 mmole) of Sigma 99+% cholesterol, 75 ml of ether (dried over activated 4A molecular sieves) and 1.214 grams (12 mmole, 1.672 ml) of dry (over KOH) triethylamine.

The flask was charged with 28 ml of dry ether and 1.84 grams (12 mmole, 1.118 ml) of phosphorous oxychloride and cooled in an ice/methanol (−10° C.) bath. Ether containing the cholesterol-triethylamine was added dropwise at a brisk rate over a period of 20–30 minutes. The solution was warmed to room temperature and stirred for 2.5 hours.

Precipitated solids were filtered off on a Buchner funnel and washed three times in water with thorough stirring. Air was introduced through the Buchner funnel until all of the ether in the filtrate evaporated. Solid precipitate was then removed by filtration through a second Buchner funnel and cholesteryl phosphodichloridate was dried in a vacuum desiccator over phosphorous pentoxide. This experiment yielded 3.90 grams (65%) of first crop solid, mp 121°–122° C. and 1.74 grams (29%) of second crop material, mp 117°–118° C. IR analysis (KBr pellet) showed (C—H) absorption at 2947 wavelengths, (=C—H) absorption at 2878 wavelengths, (C=C) absorption at 1466 wavelengths, (P=O) absorption at 1298 wavelengths and (P—O—C) absorption at 1019 wavelengths.

Ascorbic cholesteryl phosphodiester chloridate was synthesized following the procedure as outlined below.

A 50 ml three neck 19/22 ST round bottom flask fitted with a stirring bar, serum cap, nitrogen inlet needle and 50 ml dropping funnel was selected for this experiment. This apparatus was flame dried and cooled under a nitrogen sweep. The dropping funnel was charged with 503 mg (1 mmole) of cholesteryl phosphorodichloridate (mp 122° C.) and 15 ml of dry THF; and the mixture was cooled in an ice/methanol bath (−10° C.). To the cooled mixture was added 216 mg (1 mmole) of Sigma 5,6-isopropylidene-L-ascorbic acid, 15 ml of dry THF and 0.14 ml (101 mg, 1 mmole) of dry (KOH) triethylamine. After addition, the mixture was warmed to room temperature and stirred for 3 hours.

A TLC (25% methanol/toluene) analysis indicated the reaction was complete. It also suggested that the product was a mixture of 2O and 3O regioisomers. The precipitated triethylamine hydrochloride was removed by filtration through fluted paper. THF was removed by rotary evaporation to provide 0.66 grams (97%) of crude crystalline ascorbic cholesteryl phosphodiester chloridate.

Ascorbic cholesteryl phosphodiester acid was prepared utilizing the following procedure. Crude ascorbic cholesteryl phosphodiester chloridate (6.76 grams, 9.9 mmole) in 60 ml of THF was combined with 30 ml of water and 20 grams of wet Amberlyst-15 that had been rinsed in water three times. The resulting mixture was stirred vigorously at room temperature for 55 hours. Amberlyst-15 was removed by filtration through fluted paper and was rinsed once with 20 ml of 1:1 THF/water. Most of the THF was removed in a stream of nitrogen to provide 53 ml of a thick cloudy aqueous suspension.

Fifty three (53) ml of THF was added to the suspension to yield 106 ml of 1:1 THF/water solution of crude phosphodiester acid that was nearly clear. Phosphodiester acid was purified by adding the 1:1 THF/water solution to a column of C-18 reverse phase silica gel (472 grams) and eluting with 1:1 THF/water. THF was removed in a stream of nitrogen to give 215 ml of purified phosphodiester acid in aqueous suspension. The projected total yield was 1.74 grams (28%); and the actual isolated yield was 1.84 grams (30%). Reverse phase HPLC analysis indicated 90% purity.

Ascorbic cholesteryl phosphodiester diacid mono potassium salt was made by first treating a 1% aqueous solution of the diacid with one equivalent of a standardized potassium hydroxide solution and subsequent lyophilization. The phosphodiester diacid (579 mg, 0.927 mmole) was dissolved in 57.9 ml of water and treated with 9.44 ml of 0.0986 N potassium hydroxide solution (0.931 mmole). The neutralized solution was then lyophilized to remove water and yield 603 mg (98%) of mono potassium salt as a fluffy white solid.

EXAMPLE 2

Purification by Reverse Phase C-18 Chromatography

Reverse Phase C-18 silica gel was prepared on a 1 kg scale according to Evans, Chromatographia, Vol. 13, pages 5–10 (1980). Purification of the phosphodiester acid to a level of 90% was achieved at a 90:1 load ratio using 1:1 THF/water, followed by THF removal in a stream of nitrogen and water removal by lyophilization. Investigation of other solvent systems by reverse phase thin layer chromatography has good potential to (i) improve the level of purity, (ii) identify an effective separation medium that could be removed by rotary evaporation and (iii) allow the use of a lower load ratio. Since the reverse phase C-18 silica gel is reusable, the method has good potential for purification up to 1000 grams.

Solvent systems which are suitable include THF/methanol, THF/ethanol, THF/isopropanol, dioxane/methanol, dioxane/ethanol, dioxane/isopropanol, ether/methanol, ether/ethanol, ether/isopropanol, ethyl acetate/methanol, ethyl acetate/ethanol, ethyl acetate/isopropanol, methylene chloride/ethanol, methylene chloride/methanol, methylene chloride/isopropanol, DME/methanol, DME/ethanol and DME/isopropanol.

Conjugation with cholesterol converts the polar ascorbic acid to a non-polar lipophilic ascorbyl group which is readily absorbed through the stratum corneum. Once past the stratum corneum, the absorbed compound is able to effect underlying fibroblasts. The benefits of bioreversed ascorbic acid and cholesterol have been previously explained. But, surprisingly, the conjugated compound itself stimulates collagen synthesis which enhances the integrity, elasticity and resilience of skin. Additional details are provided in Example 3.

EXAMPLE 3

Fibroblast Studies

This example summarizes a study in which the ability of 31'-(L-ascorbyl-2-phosphoryl)-cholesterol to stimulate collagen production in cultured human skin fibroblasts was demonstrated. An art-recognized [$^3$H]-Proline Incorporation Assay was performed with different doses of 3'-(L-ascorbyl-2-phosphoryl)-choles-terol. Juva, Anal. Biochem., Vol. 15, pages 77–83 (1966); Booth, Biochim. Biophys. Acta, Vol. 675, pages 117–122 (1981).

Fibroblasts were incubated with 0 μg/ml, 11.3 μg/ml, 22.5 μg/ml and 45 μg/ml of 3'-(L-ascorbyl-2-phosphoryl)-cholesterol for a total of 48 hours. After the first 24 hours [$^3$H]-labeled proline was added to the culture. Following the second 24 hour period the cells were harvested and prepared for the collagen biosynthesis assay.

Protease inhibitors were added to prevent degradation of collagen and other proteins. The cell layer was scraped into a solution containing 0.4M NaCl and 0.01M Tris (pH 7.5). Extracts were sonicated to disrupt cell membranes. Separate volumes of the cell-containing solution (1 ml each) were dialyzed overnight against several changes of deionized water. The retentate was removed from dialysis and hydrolyzed in 6N hydrochloric acid at 120° C. overnight. The assay was performed using an oxidation process with 2M chloramine-T. Samples were analyzed for radioactive counts, which represent the amount of newly synthesized [$^3$H]-hydroxyproline—an index for new collagen synthesis.

It was discovered that 3'-(L-ascorbyl-2-phosphoryl)-cholesterol increased production of new collagen by human spin fibroblasts in a dose-dependent manner as illustrated by FIG. 1.

Various modifications and alterations to the present invention may be appreciated based on a review of this disclosure. These changes and additions are intended to be within the scope and spirit of this invention as defined by the following claims.

What is claimed is:

1. A topical formulation comprising:
   a suitable topical vehicle selected from the group consisting of a lotion, a cream and a gel; and
   about 0.1 to about 20.0% of a compound selected from the group consisting of 3'-(L-ascorbyl-2-phosphoryl)-cholesterol, 3'-(L-ascorbyl-3-phosphoryl)-cholesterol and salts thereof.

2. The topical formulation of claim 1, wherein said salt is selected from the group consisting of salts of ammonium, calcium, lithium, potassium, sodium and an organic amine.

3. A topical lotion formulation which comprises:
   (a) about 0.1 to about 20.0% of a compound selected from the group consisting of 3'-(L-ascorbyl-2-phosphoryl)-cholesterol and 3'-(L-ascorbyl-3-phosphoryl)-cholesterol;
   (b) about 0.5 to about 6.0% glycerin;
   (c) about 2.0 to about 8.0% propylene glycol dicaprylate/dicaprate;
   (d) about 1.8 to about 4.0% Peg 40 Stearate;
   (e) about 1.0 to about 2.5% Steareth-2;
   (f) about 0.25 to about 0.7% xanthan gum;
   (g) about 0.25 to about 0.7% hydroxyethyl cellulose;
   (h) about 0.15 to about 0.2% disodium EDTA; and
   (i) about 0.20 to about 0.25% methylparaben.

4. The topical lotion formulation of claim 3, wherein the pH of said formulation is adjusted to physiologically acceptable levels with sufficient amounts of a compound selected from the group consisting of ammonium hydroxide, calcium hydroxide, lithium hydroxide, potassium hydroxide, sodium hydroxide, ethanolamine, diethanolamine and urea.

5. A topical cream formulation which comprises:
   (a) about 0.1 to about 20.0% of a compound selected from the group consisting of 3'-(L-ascorbyl-2-phosphoryl)-cholesterol and 3'-(L-ascorbyl-3-phosphoryl)-cholesterol;
   (b) about 0.5 to about 4.0% glycerin;
   (c) about 2.0 to about 6.0% propylene glycol dicaprylate/dicaprate;
   (d) about 1.8 to about 3.0% Steareth-20;
   (e) about 0.8 to about 2.0% Steareth-2;
   (f) about 0.25 to about 0.6% xanthan gum;
   (g) about 0.25 to about 0.6% hydroxyethyl cellulose;
   (h) about 1.0 to about 2.5% cetyl alcohol;
   (i) about 0.9 to about 3.5% glycerol mono-stearate; and
   (j) about 0.15 to about 0.2% disodium EDTA.

6. The topical cream formulation of claim 5, wherein the pH of said formulation is adjusted to physiologically acceptable levels with sufficient amounts of a compound selected from the group consisting of ammonium hydroxide, calcium hydroxide, lithium hydroxide, potassium hydroxide, sodium hydroxide, ethanolamine, diethanolamine and urea.

7. A topical gel formulation which comprises:
   (a) about 0.1 to about 20.0% of a compound selected from the group consisting of 3'-(L-ascorbyl-2-phosphoryl)-cholesterol and 3'-(L-ascorbyl-3-phosphoryl)-cholesterol;
   (b) about 0.15 to about 0.2% disodium EDTA;
   (c) about 2.0 to about 6.0% propylene glycol;
   (d) about 0.4 to about 1.5% hydroxyethyl cellulose; and
   (e) about 0.20 to about 0.25% methylparaben.

8. The topical gel formulation of claim 7, wherein the pH of said formulation is adjusted to physiologically acceptable levels with sufficient amounts of a compound selected from the group consisting of ammonium hydroxide, calcium hydroxide, lithium hydroxide, potassium hydroxide, sodium hydroxide and ethanolamine.

* * * * *